United States Patent [19]

Domb et al.

[11] Patent Number: 5,486,591

[45] Date of Patent: Jan. 23, 1996

[54] BIOPOLYMERS DERIVED FROM HYDROLYZABLE DIACID FATS

[75] Inventors: Abraham J. Domb, Gush Ezion; Raphael Nudelman, Rehovot, both of Israel

[73] Assignee: Yissum Research Development Co. of the Hebrew University of Jerusalem, Jerusalem, Israel

[21] Appl. No.: 407,183

[22] Filed: Mar. 21, 1995

Related U.S. Application Data

[62] Division of Ser. No. 168,457, Dec. 16, 1993.

[51] Int. Cl.$^6$ .......................... C08G 63/02; C08G 63/44; C08G 69/00

[52] U.S. Cl. .......................... 528/272; 528/288; 528/302; 424/486

[58] Field of Search ..................... 528/272, 288, 528/302; 424/486

[56] References Cited

FOREIGN PATENT DOCUMENTS

| 0514201 | 4/1993 | European Pat. Off. . |
|---|---|---|
| 58/117289 | 8/1987 | Japan . |
| 91/03512 | 3/1991 | WIPO . |

*Primary Examiner*—Nathan M. Nutter
*Attorney, Agent, or Firm*—Kohn & Associates

[57] ABSTRACT

A monomeric diacid derivative includes at least two fatty acids coupled by a hydrolytically or enzymatically degradable bond. In a biological environment, the bond degrades forming naturally occurring fatty acid products thereby allowing elimination.

6 Claims, 3 Drawing Sheets

BIOPOLYMERS DERIVED FROM HYDROLYZABLE DIACID FATS

This a divisional of application Ser. No. 08/168,457 filed on Dec. 16, 1993.

TECHNICAL FIELD

This invention relates to the area of organic synthesis and, in particular, the synthesis of biocompatible polymers.

BACKGROUND OF THE INVENTION

Over the last 20 years, many classes of biodegradable polymers have been under development for a wide variety of biomedical applications.[1] The most actively pursued biomaterials include: the lactide/glycolide copolymers, polyorthoesters, polycaprolactones, polyphosphazenes and polyanhydrides.[1,2,3] One of the widely studied applications of these polymers is their use in implantable drug delivery systems. For this application, polyanhydrides are a unique class of polymers because some of them demonstrate a near zero order drug release and a relatively rapid biodegradation in vivo.

Some of the desired physico-chemical and mechanical properties in a single polymer that could be used in an implantable or injectable drug delivery system are:

a. hydrophobic enough so that the drug is released in a predictable and controlled way;
b. biocompatible when implanted in the target organ;
c. being completely eliminated from the implantation site in a predictable time;
d. suitable physical properties for device fabrication properties (low melting point, usually below 100° C., and soluble in common organic solvents);
e. flexible enough before and during degradation so that it does not crumble or fragment during use; and
f. easy to manufacture at a reasonable cost.

Some of these ideal properties are displayed by some of the polyanhydrides. For example, poly(carboxyphenoxy propane) [P(CPP)] displays near zero order erosion and release kinetics.[4] However, this polymer displays an extremely slow degradation rate, and it is estimated that a drug delivery device prepared from P(CPP) would take almost three years to completely degrade in vivo.

In U.S. Pat. No. 5,171,812, a class of aliphatic copolyanhydrides was synthesized from dimers and trimers of unsaturated fatty acids (FAD and FAT, respectively) with sebacic acid. This class of polymers were demonstrated to have the properties suitable for developing various types of implantable drug delivery devices, including: microspheres, films, rods, and beads.

In a recent publication,[5] a class of aliphatic copolyanhydrides was synthesized from nonlinear hydrophobic dimers (FAD) of erucic acid and sebacic acid (SA). This class had some biocompatible characteristics even though there was a rapid partial degradation within the first ten days with the release of the SA component, a residue which is mostly the FAD comonomer remains and is not easily degraded.

Although these polymers were found suitable for drug delivery applications both in vivo and in vitro, studies in dogs showed that when implanted in muscle, the polymer degraded to the synthetic fatty acid dimer which was not eliminated from the implantation site even after six months. This semisynthetic fatty acid dimer is not easily metabolized in the body because it contains a non-natural structure of a C—C bridge (Structure 1) which is difficult to be metabolized by body enzymes.

Structure 1. Fatty Acid Dimer

The FAD and related oligomers of fatty acids are the coupling products of two or more unsaturated fatty acids in which the original fatty acids are connected via a chemically stable C—C bond (non-hydrolyzable). Because the oligomerized fatty acids contain a non-natural structure (C—C branching points), they may not be eliminated at the same rate and capacity as natural fatty acids, which are readily eliminated from the body by a β-oxidation process.

SUMMARY OF THE INVENTION AND ADVANTAGES

According to the present invention, a monomeric diacid derivative comprising at least two fatty acids coupled by a hydrolytically or enzymatically degradable bond is formed. In a biological environment, the bond degrades forming naturally occurring fatty acid products thereby allowing elimination.

In general, the monomeric diacid derivative has the structure wherein R, $R^1$ and $R^2$ are aliphatic organic residues with 0 to 20 carbon atoms and can be the same or different, X is an enzymatically or hydrolytically degradable bond selected from the group consisting of ester, amide, urethane, acetal, urea, and carbonate bonds can be formed.

The absence of stable C—C nonhydroyzable branching bonds allows these monomers to be first hydrolyzed to the respective natural acids and then rapidly eliminated since naturally occurring fatty acids are formed and are readily eliminated from the body via β-oxidation.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

The present invention relates to biodegradable polymers containing novel hydrolyzable diacid fats which provide hydrophobicity and improved physical and mechanical properties to the polymers as compared to biopolymers that do not contain these monomeric units, and yet are completely degradable to natural products when exposed to biological environments.

In searching for an alternative hydrophobic monomer that possesses similar properties to the FAD but is more readily eliminated from the body, i.e. does not contain a stable C—C coupling bond, applicants have synthesized a new class of fatty-acid-based-diacid monomers with similar properties to the FAD monomer but that hydrolyze to the natural fatty acid.

The diacids were synthesized from fatty acids containing a hydroxyl or amine side group and aliphatic diacid derivatives. The general structure of these monomers is:

wherein R, $R^1$ and $R^2$ are aliphatic organic residues with 0 to 20 carbon atoms and can be the same or different, X is an enzymatically or hydrolytically degradable bond selected from the group consisting of ester, amide, urethane, acetal, urea, or carbonate bonds can be formed. Examples of other useful monomers are diacid derivatives of tartaric acid and glycerylmonostearate.

These monomers are synthesized, for example, from natural hydroxy fatty acids which are reacted with dicarboxylic acid derivatives, such as cyclic anhydrides, to provide diacid monomers suitable for anhydride and ester polymerization. The reaction is conducted in an organic solvent where the hydroxyacid is reacted under reflux with the cyclic anhydride. When other reactive acids are used, the reaction conditions should be adjusted. The natural molecules are therefore linked by an hydrolyzable bond which include: ester, amide, imide, orthoester, carbonate, urethane, urea or phosphate ester. These diacid fats can be polymerized or copolymerized into a polyanhydride or polyester and form polymers that are, in general, of a low melting point (below 100° C.), soluble in common organic solvents, and pliable materials.

This invention is demonstrated by the synthesis and characterization of polymers based on ricinoleic acid. Natural hydroxy fatty acids, such as 12-hydroxy stearic acid and ricinoleic acid were reacted with cyclic anhydrides such as succinic or maleic anhydride, to provide diacid monomers suitable for anhydride and ester polymerization. These monomers are expected to degrade in vivo into their fatty acid and succinic acid counterparts since they are bound by a hydrolyzable ester bond. The structures of the diacids are:

I. Ricinoleic acid maleate (RAM)

II. 12-Hydroxystearic acid succinate (HSAS)

III. 12-Hydroxystearic acid maleate (HSAM)

Diacids were synthesized based on Ricinoleic acid, 12-hydroxy oleic acid. The hydroxyl group was reacted with maleic anhydride to form ricinoleic acid maleate (I). Hydrogenolysis of this diacid forms the saturated derivative, 12-hydroxy stearic acid succinate (II). A third diacid monomer was synthesized from the reaction between 12-hydroxy stearic acid and maleic anhydride (III). These diacid monomers were incorporated into a polyanhydride or polyester and used as carriers for drugs.

The diacid fats used as examples in this application have the following general structures: Structure 2. Naturally occurring fatty acids containing diacid monomers

A. monoglyceride dicarboxylic acid

B. Tartaric acid dialkyl derivative

C. Dicarboxylic acid fat x=5–25; y=1–12; v+w=25; Z=CO,CO—O,CO—NH; and M=O— CO,O—CO—O,O—CO—NH, O—PO$_2$—O, NH—CO.

These monomers are diacid derivatives of monoglycerides, tartaric acid and fatty acids having an additional functional group with one or more natural molecules linked by an hydrolyzable bond which include: ester, amide, imide, orthoester, carbonate, urethane, urea or phosphate ester. These diacid fats can be polymerized or copolymerized into a polyanhydride or polyester and form polymers that are, in general, of a low melting point (below 100° C.) soluble in common organic solvents, and pliable materials that are useful in making biodegradable medical devices. For example, microspheres loaded with drugs can be prepared for the delivery of drugs in vivo and in vitro. Because these monomers hydrolyze in a biological environment to their original natural and safe counterparts, they are biocompatible and their elimination time after polymer degradation is within three months.

These monomers are polymerized into polyanhydrides and into polyesters as described in the examples.

Additionally, these diacid fats can be used as plasticizing components in plastics such as nylon, polyurethane as substitute for oligomerized fatty acids with the advantage of simple structure and ease of preparation.

The present invention allows the preparation of a drug release system which will deliver a pharmacologically effective amount of a drug. The drug is held or entrapped in a polymer matrix. The matrix essentially consists of repeating units of a monomeric diacid derivative comprising at least two fatty acids coupled by a hydrolytically or enzymatically degradable bond whereby said degradable bond in a biological environment degrades forming naturally occurring fatty acid products. As the bonds degrade the drug is released. The bonds can be ester, amide, urethane, urea and carbonate bonds.

The drugs in solid form are melted or dispersed in the polymer to form a matrix, small molecules, as well as large molecules, such as peptides, proteins, and antibodies, can be delivered from the polymer matrix. The duration of drug release is mostly affected by the hydrophobicity of the drug, drug loading, and polymer composition.

Further, the present invention can be used as a biocompatible, biodegradable, implantable material essentially consisting of repeating units of a monomeric diacid derivative comprising at least two fatty acids coupled by a hydrolytically or enzymatically degradable bond whereby said degradable bond in a biological environment degrades forming naturally occurring fatty acid products. The bonds can be ester, amide, urethane, urea and carbonate bonds. The implantable material can be used to form dressings, sutures and the like that need to be implanted but not remain in the body. For example, they can be used as films for surgical adhesion prevention by placing the polymer film at the abraded area during surgery.

In general, the method for synthesizing the biodegradable polymer containing hydrolyzable diacid fats requires the preparation of at least one highly pure prepolymer of monomeric diacid derivative comprising at least two fatty acids coupled by a hydrolytically or enzymatically degradable bond. The prepolymer is then polymerized at a temperature and reaction time to form a polyanhydride or polyester of an appropriate molecular weight. The polymerization is stopped when a molecular weight between 10,000 and 100,000 is obtained for the needed application or device.

A copolymer is formed from at least two highly pure prepolymers polymerized together as described above. U.S. Pat. No. 4,757,128 to Domb et al., issued July 1988, discloses examples of classes of monomers that can be copolymerized with the monomers of the present invention to form copolyanhydrides. Typical and useful co-monomers are the aliphatic diacid such as adipic, subernic, dodedecane dicarboxylic acid. Other co-monomers can be iso-phthalic acid terephthalic acid, carboxphenoxypropane. The copolymer of RAM with subernic acid gave a Mw of 32,000, the copolymer with iso-phthalic acid gave a Mw of 24,000.

The ricinoleic acid maleate of the present invention are useful as plasticizer for plastic modeling. The following is the preferred method of preparing the formulation.

Ricinoleic acid maleate containing plasticizer

Low volatile polyester mixtures based on Ricinoleic acid maleate are useful as plasticizer for plastic modeling:

A mixture of adipic acid (58 grams), ricinoleic acid maleate (7 grams), propylene glycol (38 grams), and n-hexanol (13 grams) was heated at 140° C. for five hours while water was distilled. To the reaction mixture, 0.05% of stannous octoate was added as catalyst and the reaction temperature was increased to 180° C. and a vacuum of 0.1 mm Hg was applied for an additional three hours. The resulting viscous polymer had a molecular weight of 700 as determined by gel permeation chromatography. The resulting oligomer was mixed 30 weight percent with polyvinylchloride (PVC) to form a flexible sheet which had a loss of 0.5 weight percent in the volatility test at 105° C. for three days compared to 1.2 to 2.5% with the phthalate plasticizer. Other plasticizers were prepared similarly using hydroxy stearic acid succinate or hydroxy stearic acid maleate instead of ricinoleic acid maleate.

Preparation of hydrophilic plasticizer: Ricinoleic acid maleate was reacted with two equivalents of poly(ethylene glycol) MW≡ 2,000 in toluene with 1% $H_3PO_4$ (85% concentration) as catalyst. The reaction was continued for five hours at 110° C. Toluene was evaporated to dryness to form an oily material. The material was mixed in PVC to form a flexible sheet which had a loss of 0.6% at 105° C. for three days volatility test.

The following examples illustrate the preparation of and use of the monomers and polymers of the present invention:

Materials and Methods

The following compounds were used: ricinoleic acid (Kodak 91% pure), maleic anhydride (BDH, 99.5%), Sebacic acid (Aldrich 99%), acetic anhydride, toluene (dried by azeotropic distillation before use), EtOH (abs.), $CH_2Cl_2$, and $CHCl_3$ (all Frutarom analytical grade).

IR spectroscopy was performed on an Analect Instruments FTIR spectrometer model fx-6160 using a Data system MAP-67. Monomer, prepolymer, and polymer samples were film cast onto NaCl plates or dissolved in chloroform and placed in a NaCl cell.

Ultraviolet spectroscopy was performed on a Kontron® Instruments Uvikon spectrophotometer model 930.

Melting points were determined on an Electrothermal melting point apparatus. Melt transition temperatures and degree of crystallinity were determined by a Perkin Elmer DSC 7 differential scanning calorimeter, calibrated with zinc and indium standards. The heating rate was 20° C./min for all the polymers, under nitrogen atmosphere.

Molecular weights of the polymers and prepolymers were estimated on a GPC system composed of a Spectra Physics P1000 pump, Applied Biosystems 759A Absorbance UV detector at 254 nm, Spectra Physics Data Jet injector, and a WINner/286 data analysis computer system. Samples were eluted in dichloromethane through a linear Styroget, $10^4$ Å pore size, at a flow rate of 1 ml/min and monitored at 254 nm. Molecular weight of polymers were determined relative to polystyrene standards (Polysciences, Pa.), with a molecular weight range of 400 to 1,500,000 using Maxima 840 computer program (Waters, Mass.).

$^1$H-NMR spectra were obtained on a Varian 300 MHz spectrometer at 23° C. using deuterated chloroform/TMS solvent. Chemical shifts were expressed in ppm downfield from Me$_4$Si as an internal standard. The values are given in d scale.

Tensile strength measurements were attained using an Instron Tensile Tester Model 1114 at room temperature.

Catalytic hydrogenation was performed using 3% Pd on activated carbon (Aldrich) using a Parr apparatus. Evaporation's were carried out on a Buchi RE 111 Rotavapor.

EXAMPLES

1. Monomer and Polymer Synthesis

Ricinoleic acid maleate (RAM). A solution of ricinoleic acid (144 g, 0.48 mol) and maleic anhydride (61 g, 0.61 mol) in toluene (350 ml) was stirred at 80°–90° C. overnight. The excess of maleic anhydride which precipitated was removed by filtration. The solution was washed four times with distilled water, dried over MgSO$_4$ and evaporated to dryness to give 140.92 g (73%) of product as a dark orange oil. Titration (using THF as solvent and phenolphthalein as indicator) with 0.1N NaOH showed 88% diacid product; IR 1740, 1715 cm$^{-1}$; $^1$H-NMR 6.33 (dd, 2H, HOOC—CH=CH—COO—), 5.45 (m, 1H, C—CH=CH—C), 5.28 (m, 1H, C—CH=CH—C), 5.00 (quintet, 1H, methine), 2.33 (m, 2H, CH$_2$—COOH), 2.00 (dd, 2H, OCO—C—CH$_2$—CH=CH), 1.60 (m, 4H, CH$_2$—COOH and COO—CH—CH$_2$—CH$_2$), 1.25 (broad d, 18H, aliphatic methylenes), 0.83 (t, 3H, —CH$_3$)

12-hydroxysteric acid succinate (HSAS). A solution of RAM (50 g. 0.13 mol) in abs. EtOH (~100 ml) was hydrogenated over 3 g Pd/C at 85 atm overnight. The catalyst was filtered off, and the solution was evaporated to dryness yielding 46.83 g (94%) of an oily orange liquid, which upon cooling to room temperature solidified to an off-white solid which was dissolved in hot EtOH and left to recrystallize in the freezer for two weeks. The product was filtered and dried to give 37.0 g (74%), mp 50°–52° C.; IR 1740, 1715 cm$^{-1}$; $^1$H-NMR 4.88 (quintet, 1H, methine), 2.77 (t, 2H, HOCO—CH$_2$—CH$_2$—COO—CH), 2.63 (t, 2H, HOCO—CH$_2$—CH$_2$—COO—CH) 2.42 (t, 2H, CH$_2$—COOH), 1.62 (m, 4H, CH$_2$—CH—OCO—CH$_2$), 1.52 (m, 2H, CH$_2$—CH$_2$—COOCO), 1.23 (m, 22H, aliphatic methylenes), 0.85 (t, 3H, CH$_2$—C$_3$)

12-hydroxystearic acid maleate (HSAM). A solution of ricinoleic acid (50 g, 0.17 mol) in abs. EtOH (~100 ml) was hydrogenated over 3 g Pd/C at 80 atm overnight. The solidified product was dissolved in CH$_2$Cl$_2$, and the catalyst was removed by filtration. The solution was evaporated yielding 50 g (100%) of product. Recrystallization from EtOH gave 35.0 g (70%). The FTIR and NMR spectra were similar to those described in the Aldrich 93 catalogs, mp 73°–75° C. (lit: Aldrich 93 catalog 80°–81° C.). A solution of 12-hydroxystearic acid (34.45 g, 0.11 mol) and maleic anhydride (14.5 g, 0.148 mol) in toluene (240 ml) was stirred at 88° C. overnight. The solution was washed four times with distilled water, dried over MgSO$_4$ and evaporated to dryness to yield 40.0 g (88%). Titration (using THF as solvent and phenolphthalein as indicator) with 0.1N NaOH showed 96% diacid product; IR 1740, 1715 cm$^{-1}$; $^1$H-NMR 6.38 (d, 2H, COCH=CHCO), 5.02 (t, 1H, CHOCO), 2.36 (t, 2H, CH2COOH), 1.61 (m, 6H$_2$CCOCHO and CH$_2$CH$_2$COOH), 1.27 (m, 22H, (CH$_2$)$_{11}$), 0.88 (t,3H,CH$_3$).

Preparation of prepolymers. The prepolymers of sebacic acid (SA) were prepared as previously described.$^6$ Briefly, sebacic acid prepolymer was prepared from the purified diacid monomer by refluxing it in excess acetic anhydride for 30 minutes and evaporating it to dryness. The hot clear viscous residue was dissolved in dichloromethane and the prepolymer was precipitated in a mixture of hexane/isopropyl ether (1:1). The solid was collected by filtration and dried by vacuum at room temperature.

Prepolymers of the fatty acid ester based monomers were prepared as follows: Solutions of each monomer dissolved in acetic anhydride (120° C., 1:5 w/v) were stirred under reflux for 20 min.

The RAM prepolymer solution was evaporated to dryness to give an orange oil product. Mw-3800 Mn-3520; IR 2900, 2850, 1810, 1720 cm$^{-1}$; $^1$H-NMR 6.30 (dd, 2H, CO—CH=CHCO), 5.42 (d, 1H, CH=CH), 5.38 (d, 1H, CH=CH), 4.98 (quintet, 1H, methine), 2.45 (t, 2H when prepolymer is head-to-tail, CH$_2$—COO—), 2.40 (t, 2H when prepolymer is head-to-head, CH$_2$—COO—), 2.32 (s, 3H, CH$_3$—COOCO—CH=CH), 2.21 (s, 3H, CH$_3$—COOCO—CH$_2$—CH$_2$), 2.00 (dd, 2H, C—CH$_2$—CH=CH), 2.30 (m, 2H, CH=CH—CH$_2$—CH$_2$—) 1.60 (m, 4H, CH$_2$—CH$_2$—COOCO—and CH=CH—COO—CH—CH$_2$—CH$_2$), 1.30 (broad d, 16H, aliphatic methylenes), 0.87 (t, 3H, CH$_2$—CH$_3$). The HSAS prepolymer gave a semisolid off-white product. Mw-1788 Mn-1382; IR 2900, 2850 1820, 1730 cm$^{-1}$; $^1$H-NMR 4.88 (quintet, 1H, methine), 2.77 (t, 2H, COOCO—CH$_2$—CH$_2$—COO—CH), 2.65 (t, 2H, COOCO—CH$_2$—CH$_2$—COO—CH), 2.44 (t, 2H, CH$_2$—COOCO), 1.65 (m, 4H CH$_2$—CH—OCO—CH$_2$), 1.55 (quintet, 2H, CH$_2$—CH$_2$—COOCO) 1.25 (m, 22H, aliphatic methylenes), 0.85 (t, 3H, CH$_2$—CH$_3$).

The HSAM prepolymer gave a viscous oil. Mw-1788 Mn-1382; IR 2900, 2850, 1820, 1730 cm$^{-1}$, $^1$H- NMR 6.26 (dd, 2H, CO—CH=CH—CO), 4.92 (quintet, 1H, methine), 2.47 (t, 2H when prepolymer is head-to-tail, CH$_2$—COO—), 2.40 (t, 2H when prepolymer is head-to-head, CH$_2$—COO—) , 2.25 (s, 3H, CH$_3$—COOCO—CH=CH), 2.17 (s, 3H, CH$_3$—COOCO—CH$_2$—CH$_2$), 1.52 (m, 4H, CH$_2$—CH$_2$—COOCO—and CH=CH—COO—CH—CH$_2$—CH$_2$ ), 1.21 ( broad, d, 22H, aliphatic methylenes), 0.83 (t, 3H, CH$_2$—CH$_3$).

Preparation of polymers. The prepolymers underwent melt polycondensation. Typically, RAM prepolymer (10 g, 33 mmol) was placed in a KIMAX® glass tube with a side arm or a round bottomed flask and polymerized at 180° C. under reduced pressure (0.1–0.5 mm Hg). The polymerization was complete after 90 minutes. The by-products, acetic anhydride and acetic acid, were trapped in a liquid N$_2$ trap. The homopolymers were viscous yellow oils.

Copolymers were prepared similarly by polymerizing a mixture of prepolymers at 180° C. under reduced pressure. In a typical experiment, RAM prepolymer (5 g, 17 mmol) was mixed with sebacic acid prepolymer (SA-diAc) (5 g, 21mmol) and polymerized at 180° C. under reduced pressure for 60–90 minutes depending on the amount being polymerized. The crude polymers were dissolved in CH$_2$Cl$_2$ (1.5 w/v) and filtered into stirring di-isopropyl ether (100–200 ml). The precipitate was separated by filtration, washed with di-isopropyl ether, and dried in the Rotavapor.

Molecular weights and thermal characterization of the polymers are shown in Table 1. The IR and $^1$H-NMR of homopolymers of RAM,HSAM,HSAS, and 1:1 copolymers with SA (d ppm) are listed in Table 2.

Mechanical Properties. These series of polymers had similar mechanical properties to the FAD class of polymers. They formed very flexible films with similar strength as seen in Table 3.

2. Synthesis of polyesters containing fatty diacid monomers. Biodegradable polyesters were synthesized from the reaction between lactide, ricinoleic acid maleate, and propylene glycol in the molar ratio 8:1:1 and 1% stannous octoate as polymerization catalyst. The mixture of the monomers were polymerized at 100° C. under nitrogen with constant stirring. After 24 hours, the temperature was raised to 140° C., the reaction was continued for another 24 hours and then a vacuum of 0.1 mm Hg was applied and the reaction was continued for another 8 hours. The viscous melt was solidified into a pliable tan mass. Polymers containing HSAM and HSAS monomers at various ratios were prepared similarly. The data analysis of these polymers is summarized in Table 4. All polymers were soluble in dichloromethane, chloroform, and tetrahydrofuran. IR spectra of the polymers showed esters peaks at 1720 nm.

3. Synthesis of distearyl tartaric acid. Into a flask were placed 100 ml dichlomethane, tartaric acid (0.1 mole), triethylamine (0.4 mole), and stearoyl chloride (0.2 mole). The reaction was left for 24 hours with constant stirring. The reaction mixture was washed with 0.1N HCl solution to yield distearyl tartaric acid.

4. In vivo biocompatibility and elimination studies. The biocompatibility and the elimination time of these new polymers as compared to poly(FAD-SA) 50:50 and poly-(sebacic acid) {PSA} was studied in rats as follows:

Clean specimens (30 mg, 2×2×4 mm in size) of the following polymers:
1. poly(RAM-SA) 30:70,
2. poly (HSAM-SA) 50:50,
3. poly(HSAS-SA) 50:50,
4. poly (FAD-SA) 50:50,
5. Vicril (Ethicon),
6. poly(FAD-SA)50:50, and
7. poly(sebacic acid) {PSA} implanted subcutaneously in four dorsal sites of male Sprague-Dawley rats (250–300 g). Six rats were used in the study and each rat was implanted randomly with four different specimens. All animal work was done under sterile conditions. The polymer specimens were dipped in 70% alcohol prior to insertion. The animals were sacrificed after 12 and 30 days post implantation, and the implantation sites were examined macroscopically and histologically. The polymer remnants were retrieved and analyzed.

Macroscopically, no swelling or pathological signs were observed in any of the groups during the experiment and at sacrifice. The animals appeared healthy and did not show any weight loss. The implantation sites were clean and normal without any swelling and the remnants of the implanted polymers were easily retrieved. At the implant site of the new polymers, a small amount of polymer remnants (30–40% of the original mass) in the form of a soft mass was seen. The animals implanted with poly(FAD-SA)50:50 had solid remnants in the site of about 70% of the original implant size. About 20% of the PSA remained at the implant site after 12 days, and the Vicril polymer remained intact. Histopathology examination of tissue specimens from the area confined to the tissue in direct contact with the polymer device showed mild inflammation which was rated 2 in a scale from 1 to 5 where: 1— resembles no irritation; 2—slight inflammation; 3—moderate; 4—marked; and 5—severe inflammation. No encapsulation was found with any of the samples.

A second group of rats which were implanted with the polymers under similar conditions were completely eliminated from the site after 12 weeks. In comparison, Vicril polymers remained almost intact, Poly(FAD-SA)50:50 was only 60% eliminated.

This experiment indicates that the new fatty acid based polymers are biocompatible. The elimination time in vivo of these polymers is shorter than for the FAD-based polymers.

The rat model has been considered highly predictable of human response for toxicant elimination[7] and biocompatibility.[8]

5. In vitro hydrolysis. The hydrolysis of the 1:1 copolymers with SA was studied by:

(a) weight loss of the sample;
(b) monitoring the change of molecular weight by gel permeation chromatograph (GPC);
(c) monitoring the disappearance of the anhydride linkage and the formation of carboxylic acid by FTIR spectroscopy; and
(d) the release of sebacic acid from the polymer by HPLC analysis.

Figure 1:
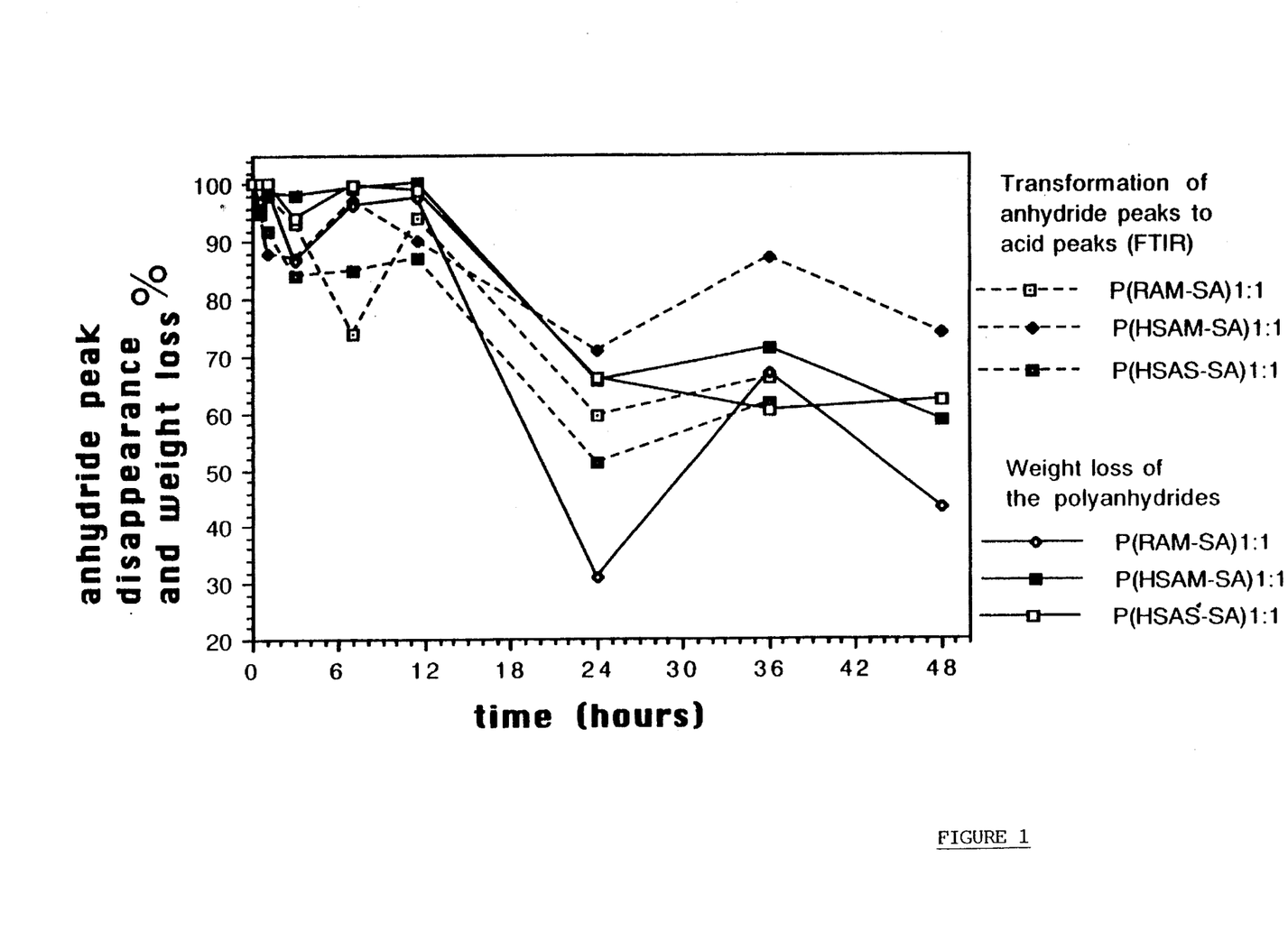
FIG. 1 is a graph showing hydrolytic degradation of polymers based on ricinoleic acid as determined by weight loss and conversion of anhydride to acid groups, degradation being determined in 0.1M phosphate buffer pH 7.4 at 37° C.

The hydrolysis studies were conducted in 0.1M phosphate buffer pH 7.4 at 37° C. using rectangular samples 3×5×8 mm in size and weighing about 100–150 mg. The samples were taken out from the buffer at different time intervals and were weighed after being dried thoroughly in the oven. The percent weight loss of the sample and the transformation of the anhydride bond to acid as a function of time are shown in FIG. 1. The change in molecular weight was monitored by GPC showing a drastic drop in molecular weight in the first 24 hours and then stabilized at about 6,000–7,000 from then on. The samples were observed visually for the changes in the external appearance. At any stage of the experiment, the samples did not crumble nor were there any cracks visible.

6. In vitro enzymatic degradation. The enzymatic degradation of these new monomers were compared to those of the oligomerized fatty acids. The monomers RAM, HSAM, HSAS, FAD, and FAT (200 mg) were mixed in a solution containing esterase (2 ml, containing 50 units of esterase from porcine liver, Sigma Chemical Company, St. Louis, Mo.) and were incubated for 24 hours at 37° C. The monomers or their degradation products were extracted with chloroform and analyzed by $^1$H NMR. The $^1$H NMR spectra of the FAD and FAT monomers were identical before and after treatment. The RAM, and HSAS monomers contained about 10% ricinoleic acid or 12-hydroxy stearic acid, respectively. This study demonstrates the biodegradability of the new monomers compared to the oligomerized fatty acid monomers.

Figure 2:
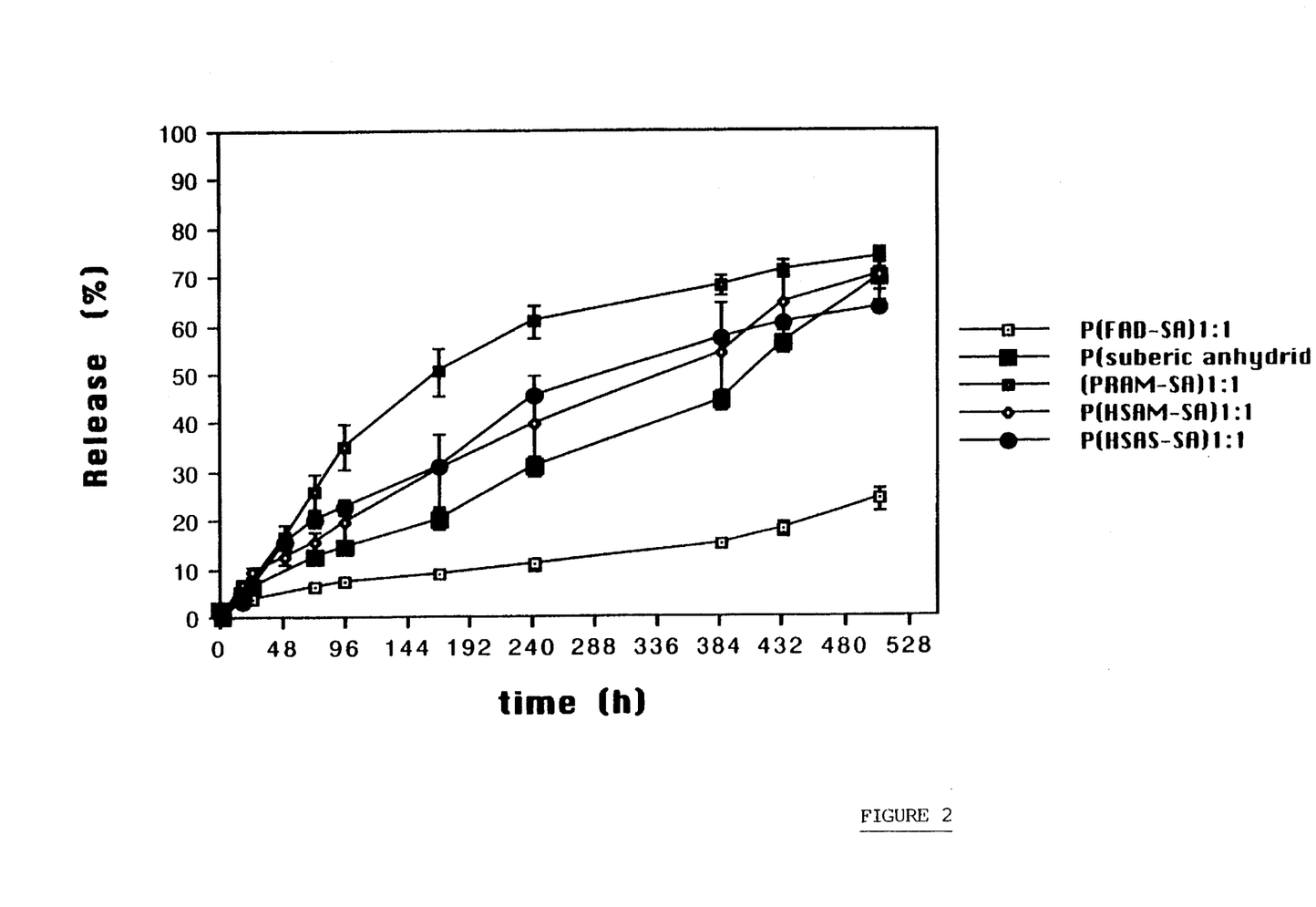
FIG. 2 is a graph showing in vitro release of ciprofloxacin from ricinoleic acid maleate-based polymeric devices, drug release being determined in 0.1M phosphate buffer pH 7.4 at 37° C.

7. In vitro drug release. Ciprofloxacin (5% by weight) was incorporated in rectangular tablets (3×5×8 mm in size and 200 mg weight) of poly (RAM-SA) 1:1, P(HSAM:SA) 1:1, P(HSAS:SA) 1:1, P(FAD:SA) 1:1 and poly(suberic anhydride) by the melt method. In vitro drug release was determined in phosphate buffer pH 7.4 at 37° C. Ciprofloxacin concentration was determined by UV detection at 272 nm. The results are shown in FIG. 2. The drug release followed a first order kinetics ($r^2=0.89-0.99$) with a fast release during the first 10 days and a slow release thereafter.

Figure 3:
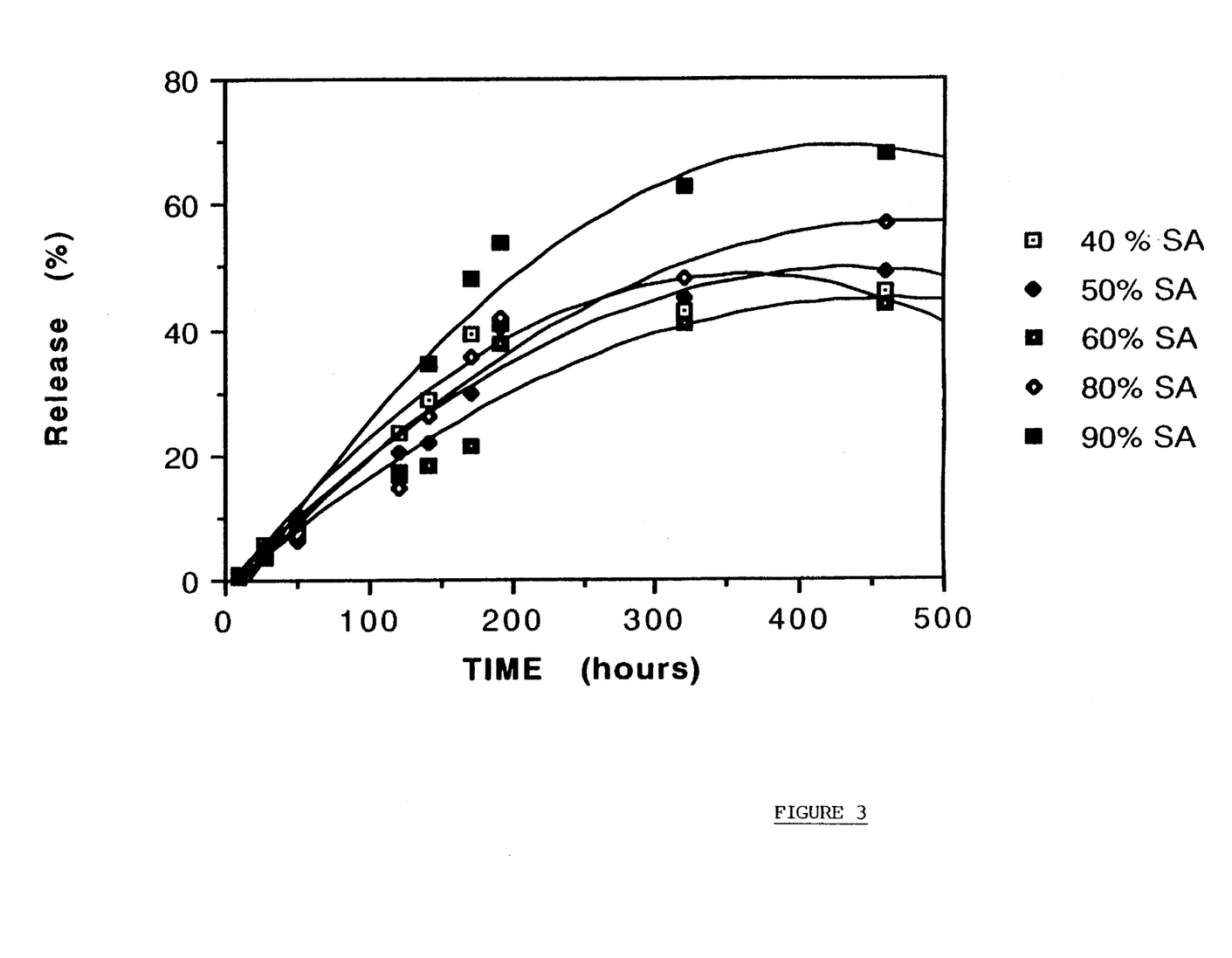
FIG. 3 is a graph showing in vitro release of ciprofloxacin from ricinoleic acid maleate-sebacic acid copolymer based polymeric devices, drug release being determined in 0.1M phosphate buffer pH 7.4 at 37° C.

In a second experiment, Ciprofloxacin (5% weight) was incorporated in rectangular tablets (3×5×8 mm in size and 20 mg weight) of poly(RAM-SA) of various compositions by the melt method. In vitro drag release was determined in phosphate buffer pH 7.4 at 37° C. Ciprofloxacin concentration was determined by UV detection at 272 nm. The results are shown in FIG. 3. The drug release followed a first order kinetics ($r^2=0.96$) with a fast release during the first 10 days and a slow release thereafter. The drug release rate was increased with the increase in the sebacic acid content in the polymer; however, a small difference in the release profile was found for the polymers composed of 40 to 80% sebacic acid (SA). Similar results were reported for the FAD-SA copolymers.

The preparation of dimer oleic acid or dimer erucic acid (FAD) contains two steps. In the first step, oleic acid or erucic acid undergo a coupling reaction using clay as a catalyst. In the second step, the product is hydrogenated to saturate the double bonds in the product. During the first step, many by-products are formed, including trimers and tetramers, that are difficult to remove. Also, the FAD product contains cyclic and aromatic by-products which counts to about 30% of the Priipol 1004 and 1009 products which are the most available pure FAD products (based on producer, Unicema, information). The product of the present invention contains only one component, the linear diacid monomer which is synthesized in a single esterification step (condensation reaction in general) which cannot form other oligomers or cyclic materials, but the linear diacid as described herein.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

TABLE 1

Molecular weights and thermal characterization of fatty acid ester polymers

| Polymer of | Molecular weight Mw | Molecular weight Mn | Melting point[b] (°C.) | $Tm^c$ $T_{max}$ (°C.) | $\Delta H^d$ (J/gm) |
|---|---|---|---|---|---|
| RAM | 27,800 | 11,400 | viscous oil | — | — |
| HSAM | 29,500 | 9,400 | semisolid | — | — |
| HSAS | 15,200 | 8,700 | semisolid | — | — |
| RAM:SA 10.90 | 10,500 | 7,200 | 72–76 | 86.18 | 98.59 |
| RAM:SA 20:80 | 8,500 | 6,200 | 68–74 | 81.33 | 108.99 |
| RAM:SA 30:70 | 14,000 | 10,800 | 68–70 | 79.33 | 103.02 |
| RAM:SA 40.60 | 6,200 | 5,000 | 65–70 | 76.63 | 65.81 |
| RAM:SA 50:50 | 135,200 | 12,900 | 56–62 | | |
| HSAM:SA 50:50 | 32,000 | 11,600 | 65–68 | 67.31 | 50.59 |
| HSAS:SA 50:50 | 28,700 | 13,000 | 68–70 | 70.39 | 78.45 |
| PSA | 465,800 | 23,400 | 83 | 88.64 | 131.88 |

[a]Polymers synthesized by melt condensation.
[b]Melting points determined on an Electrothermal melting point apparatus.
[c]Melting transition temperature determined by DSC.
[d]Degree of crystallinity is obtained from the $\Delta H$ determined by DSC, larger $\Delta H$ values insunuate higher degree of crystallinity.

TABLE 2

Other characteristics of polymers

IR. All polymers had typical IR peeks at 2900, 2850, 1805, and 1740 $cm^{-1}$
$^1$H-NMR of homopolymers of RAM, HSAM, HSAS, and 1:1 copolymers with SA (d ppm)
PRAM: 6.27 (dd, 2H, CO—CH=CH—CO), 5.43 (m, 1H, CH=CH), 5.31 (m, 1H, CH=CH), 4.96 (m, 1H, methane), 2.47 (t, 2H when prepolymer is head-to-tail, $CH_2$—COO—), 2.42 (t, 2H when prepolymer is head-to-head, $CH_2$—COO—), 2.30 (m, 2H, CH=CH—$CH_2$—$CH_2$—), 2.00 (dd, 2H, CH—$CH_2$—CH=CH), 1.60 (m, 4H, $CH_2$—$CH_2$—COOCO— and CH=CH—COO—CH—$CH_2$—$CH_2$), 1.29 (brd, 16H aliphatic methylenes), 0.88 (t, 3H, $CH_2$—$CH_3$).
PHSAS: 4.88 (quintet, 1H, methine), 2.76 (t, 2H, COOCO—$CH_2$—$CH_2$—COO—CH), 2.64 (t, 2H, COOCO—$CH_2$—$CH_2$—COO—CH), 2.43 (t, 2H, $CH_2$—COOCO), 1.65 (m, 4H, $CH_2$—CH—OCO—$CH_2$), 1.51 (brrm, 2H, $CH_2$—$CH_2$—COOCO), 1.25 (m, 22H, aliphatic methylenes), 0.88 (t, 3H, $CH_2$—$CH_3$).
PHSAM: 6.30 (dd, 2H, CO—CH=CH—CO), 4.98 (quintet, 1H, methine), 2.52 (t, 2H when prepolymer is head-to-tail, $CH_2$—COO—), 2.42 (t, 2H when prepolymer is head-to-head, $CH_2$—COO—), 1.58 (m, 4H, $CH_2$—$CH_2$—COOCO— and CH=CH—COO—CH—$CH_2$—$CH_2$), 1.24 (brd, 22H, aliphatic methylenes), 0.83 (4 3H, $CH_2$—$CH_3$).
P(RAM-SA) 1:1 : 6.27 (s, 2H, CO—CH=CH—CO), 5.45 (brm, 1H, COOCO—CH=CH—COO—CH), 5.33 (brm, 1H, COOCO—CH=CH—COO—CH), 4.98 (brm, 1H methine), 2.53 (t, 2H when RAM prepolymer is head-to-tail, $CH_2$—COO—), 2.44 (t, 2H when RAM prepolymer is head-to-head, $CH_2$—COO—), 2.35 (m, 2H, —O—CH—$CH_2$—CH=CH—$CH_2$—), 2.09 (dd, 2H, —O—CH—$CH_2$—CH=CH—), 1.65 (m, 4H, $CH_2$—$CH_2$—COOCO— and CH=CH—COO—CH—$CH_2$—$CH_2$), 1.29 and 1.25 (two brs, aliphatic methylenes from RAM and from SA), 0.87 (t, 3H, $CH_2$—$CH_3$).
P(HSAS-SA) 1:1 : 4.88 (quintet, 1H methine), 2.77 (t, 2H, COOCO—$CH_2$—$CH_2$—COO—

TABLE 2-continued

Other characteristics of polymers

CH), 2.66 (t, 2H COOCO—CH$_2$—CH$_2$—COO—CH), 2.44 (t, 6H CH$_2$—COOCO), 1.65 (m, 6H, CH$_2$—CH—OCO—CH$_2$), 1.51 (brm, 4H, CH$_2$—CH$_2$—COOCO), 1.32 (m, 12H, CH$_2$—CH$_2$—CH$_2$—CH$_2$—COO), 1.25 (m, aliphatic methylenes), 0.88 (t, 3H, CH$_2$—CH$_3$).
P(HSAM-SA) 1:1 : 6.30 (brm, 2H, CO—CH=CH—CO), 4.98 (brm, 1H, methine), 2.44 (t, CH$_2$—COO—), 1.62 (tt, 2H, CH$_2$—CH$_2$—COOCO—), 1.56 (dt, 4H, —CH$_2$—COO—CH—CH$_2$—(CH$_2$)$_4$—CH$_3$ and —CH$_2$—COO—CH—CH$_2$—(CH$_2$)$_9$—COO—), 1.32 and 1.25 (two brd, aliphatic methylenes from HSAM and from SA), 0.88 (t, 3H, CH$_2$—CH$_3$).

TABLE 3

Mechanical properties of fatty acid polymers

| Polymer composition | Mw | Mn | Tensile Strength (MPa) | Compression at break (%) |
|---|---|---|---|---|
| P(RAM-SA) 1:1 | 135,200 | 5,300 | 3.2 | buckled before breaking |
| P(HSAM-SA) 1:1 | 4,300 | 2,100 | 2.7 | 22.95 |
| P(HSAS-SA) 1:1 | 9,400 | 3,300 | 2.5 | 20.91 |
| P(FAD-SA) 1:1 | 73,000 | 5,900 | 5.7 | 9.75 |
| PSA | 18,600 | 5,800 | 7.2 | 1.57 |

TABLE 4

Data analysis for diacid fat containing lactide copolymers

| Polymer | Viscosity (dL/gr) | Melting point (°C.) |
|---|---|---|
| P(LA-RAM-PG) 8:1:1 | 0.22 | 42–47 |
| P(LA-HSAM-PG) 8:1:1 | 0.15 | 38–45 |
| P(LA-HSAS-PG) 8:1:1 | 0.20 | 47–50 |

REFERENCES

1. Domb et al., Polymeric Biomaterials, NY (in press)
2. Domb et al., Polym. Adv. Technol. (in press)
3. Domb et al., Biopolymers (in press)
4. Leong et al., Biomed. Mat. Res, 19:941 (1985)
5. Domb and Maniar (1993) J. Polymer Sci.:Part A:Polymer Chem. 31:1275–1285
6. Domb and Langer (1987) J. Polym. Sci. Part A: Polym. Chem., 1987, 25:3373
7. Ratacliffe et al. (1984) J. Pharm. Pharmacol. 36:431
8. Laurencin et al. (1990) J. Biomed. Mat. Res, 24:1463

We claim:

1. A polymer essentially consisting of repeating units of a monomeric diacid derivative comprising at least two fatty acids coupled by a hydrolytically or enzymatically degradable bond whereby said degradable bond in a biological environment degrades forming naturally occurring fatty acid products.

2. The hydrolytically or enzymatically degradable bond of claim 1 selected from the group consisting of ester, amide, urethane, urea and carbonate bonds.

3. A drug release system comprising
a pharmacologically effective amount of a drug and
a polymer matrix essentially consisting of repeating units of a monomeric diacid derivative comprising at least two fatty acids coupled by a hydrolytically or enzymatically degradable bond whereby said degradable bond in a biological environment degrades forming naturally occurring fatty acid products
wherein said drug is entrapped within said matrix and releasable upon degradation of said degradable bond.

4. The hydrolytically or enzymatically degradable bond of claim 3 selected from the group consisting of ester, amide, urethane, urea and carbonate bonds.

5. A biocompatible, biodegradable, implantable material essentially consisting of repeating units of a monomeric diacid derivative comprising at least two fatty acids coupled by a hydrolytically or enzymatically degradable bond whereby said degradable bond in a biological environment degrades forming naturally occurring fatty acid products.

6. The hydrolytically or enzymatically degradable bond of claim 5 selected from the group consisting of ester, amide, urethane, urea and carbonate bonds.

* * * * *